United States Patent

Flanagan et al.

[11] Patent Number: 5,989,810
[45] Date of Patent: Nov. 23, 1999

[54] SCREENING METHODS FOR IMMUNOSUPPRESSIVE AGENTS

[75] Inventors: William M. Flanagan, Menlo Park; Gerald R. Crabtree, Woodside, both of Calif.

[73] Assignee: Board of Trustees of Leland Stanford Jr. University, Stanford, Calif.

[21] Appl. No.: 08/507,032

[22] Filed: Jul. 31, 1995

Related U.S. Application Data

[63] Continuation of application No. 08/228,944, Apr. 18, 1994, abandoned, which is a continuation of application No. 07/749,385, Aug. 22, 1991, abandoned.

[51] Int. Cl.⁶ .............................. C12Q 1/68; C12P 19/34; G01N 33/53; C07H 21/04
[52] U.S. Cl. .............................. 435/6; 435/7.1; 435/91.5; 435/240.2; 435/172.3; 536/24.1; 436/63; 436/501; 935/6; 935/17; 935/36; 935/78; 935/77
[58] Field of Search ............................ 435/6, 7.1, 240.2, 435/172.3, 91.5; 436/501, 63; 536/24.1; 935/6, 17, 36, 77, 78

[56] References Cited

FOREIGN PATENT DOCUMENTS

| | | |
|---|---|---|
| 87/04170 | 7/1987 | WIPO . |
| 8704170 | 7/1987 | WIPO . |
| 88/05083 | 7/1988 | WIPO . |
| 89/07614 | 8/1989 | WIPO . |
| 89/08147 | 9/1989 | WIPO . |

OTHER PUBLICATIONS

Verwiej et al J. Biol Chem (1990) 265:15788–15795.

Sambrook et al, Molecular Cloning: A Laboratory Manual, 1989, Cold Spring Harbor Laboratory Press, NY, pp. 10.31–10.33.

Sawadogo et al, Cell (1985) 43:165–175.

Emmel et al Science (1989) 246:1617–1619

Shaw et al. Science (1988) 241:202–205.

Primary Examiner—W. Gary Jones
Assistant Examiner—Carla Myers

[57] ABSTRACT

Activation of NF-AT-dependent transcription, including agents which interfere with the production, modification of the nuclear or cytoplasmic subunits, or the nuclear import of the cytoplasmic subunits. In particular, screening tests for novel immunosuppressants are provided based upon the ability of NF-AT to activate transcription.

7 Claims, 12 Drawing Sheets

FP J+ J- K+ K- F+ F- H T E C J- J+

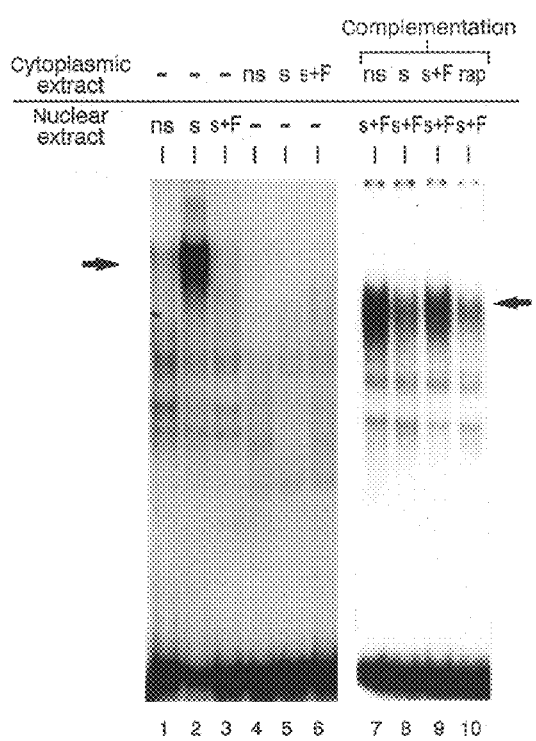
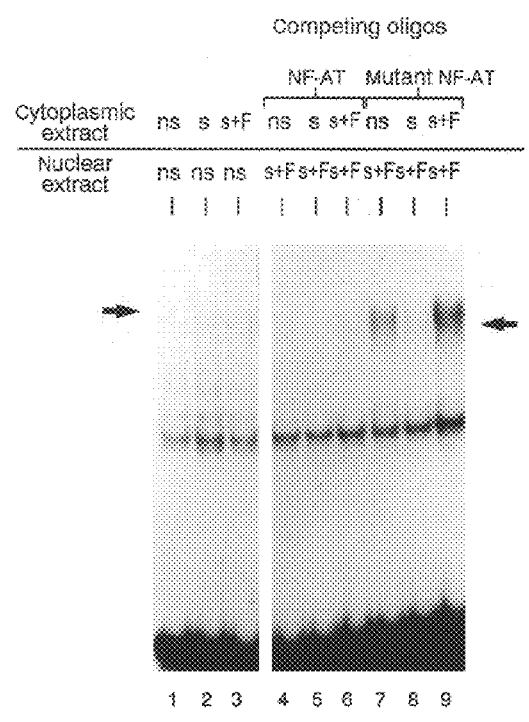
FIG. 6A
FIG. 6B

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_feature
      (B) LOCATION: 1..11
      (D) OTHER INFORMATION: /note= "Enhancer Homolog"

(xi) SEQUENCE DESCRIPTION: SEQ ID NO:1:

AAGAGGAAAA A                                                        11

(2) INFORMATION FOR SEQ ID NO:2:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ii) MOLECULE TYPE: DNA (genomic)

```
        (ix) FEATURE:
              (A) NAME/KEY: misc_feature
              (B) LOCATION: 1..11
              (D) OTHER INFORMATION: /note= "NF-AT DNA binding site"

(xi) SEQUENCE DESCRIPTION: SEQ ID NO:2:

AAGAGGAAAA A                                                            11

(2) INFORMATION FOR SEQ ID NO:3:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(ix) FEATURE:
              (A) NAME/KEY: misc_feature
              (B) LOCATION: 1..20
              (D) OTHER INFORMATION: /note= "Purine Rich Core Sequence"

(xi) SEQUENCE DESCRIPTION: SEQ ID NO:3:

GAAAGGAGGA AAAACTGTTT                                                   20

(2) INFORMATION FOR SEQ ID NO:4:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(ix) FEATURE:
              (A) NAME/KEY: misc_feature
              (B) LOCATION: 1..20
              (D) OTHER INFORMATION: /note= "Purine Rich Core Sequence"

(xi) SEQUENCE DESCRIPTION: SEQ ID NO:4:

CCAAAGAGGA AAATTTGTTT                                                   20

(2) INFORMATION FOR SEQ ID NO:5:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(ix) FEATURE:
              (A) NAME/KEY: misc_feature
              (B) LOCATION: 1..20
              (D) OTHER INFORMATION: /note= "Purine Rich Core Sequence"

(xi) SEQUENCE DESCRIPTION: SEQ ID NO:5:

CAGAAGAGGA AAAATGAAGG                                                   20

(2) INFORMATION FOR SEQ ID NO:6:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)
```

```
    (ix) FEATURE:
         (A) NAME/KEY: misc_feature
         (B) LOCATION: 1..20
         (D) OTHER INFORMATION: /note= "Purine Rich Core Sequence"

(xi) SEQUENCE DESCRIPTION: SEQ ID NO:6:

TCCAGGAGAA AAAATGCCTC                                             20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: misc_feature
         (B) LOCATION: 1..20
         (D) OTHER INFORMATION: /note= "Purine Rich Core Sequence"

(ix) FEATURE:
         (B) LOCATION: 9
         (C) OTHER INFORMATION: /note= "Base is inosine"

(xi) SEQUENCE DESCRIPTION: SEQ ID NO:7:

AAAACTTGNG AAAATACGTA                                             20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: misc_feature
         (B) LOCATION: 1..20
         (D) OTHER INFORMATION: /note= "Purine Rich Core Sequence"

(xi) SEQUENCE DESCRIPTION: SEQ ID NO:8:

TAAAGGAGAG AACACCAGCT                                             20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: misc_feature
         (B) LOCATION: 1..20
         (D) OTHER INFORMATION: /note= "Purine Rich Core Sequence"

(xi) SEQUENCE DESCRIPTION: SEQ ID NO:9:

GCAGGGTGGG AAAGGCCTTT                                             20

(2) INFORMATION FOR SEQ ID NO:10:

(i) SEQUENCE CHARACTERISTICS:
        (A) LENGTH: 33 base pairs
        (B) TYPE: nucleic acid
```

(C) STRANDEDNESS: single
        (D) TOPOLOGY: linear (ii) MOLECULE TYPE: DNA (genomic)

(xi) SEQUENCE DESCRIPTION: SEQ ID NO:10:

GATCGGAGGA AAAACTGTTC ATACAGAAGG GGT                    33

(2) INFORMATION FOR SEQ ID NO:11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GATCAAGAAA GGAGTAAAAA TTTTTAATAC AGAA                   34

(2) INFORMATION FOR SEQ ID NO:12:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

AAAGAGGAAA AT                                           12

(2) INFORMATION FOR SEQ ID NO:13:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GAAGAGGAAA AA                                           12

(2) INFORMATION FOR SEQ ID NO:14:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CAGGAGAAAA AA                                           12

(2) INFORMATION FOR SEQ ID NO:15:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

AACTTGTGAA AA                                                              12

(2) INFORMATION FOR SEQ ID NO:16:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

AAGGAGAGAA CA                                                              12

(2) INFORMATION FOR SEQ ID NO:17:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

AGGGTGGGAA AG                                                              12

(2) INFORMATION FOR SEQ ID NO:18:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

AAGAGGAAAA A                                                               11

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..30
        (D) OTHER INFORMATION: /note= "IL-2 Gene"

(xi) SEQUENCE DESCRIPTION: SEQ ID NO:19:

GGAGGAAAAA CTGTTTCATA CAGAAGGCGT                                           30

SCREENING METHODS FOR IMMUNOSUPPRESSIVE AGENTS

This is a Continuation of application Ser. No. 08/228,944, filed Apr. 18, 1994, now abandoned, which is a Continuation of application Ser. No. 07/749,385, filed Aug. 22, 1991, now abandoned.

This invention was made in the course of work supported by the U.S. Government, which has certain rights in this invention.

BACKGROUND OF THE INVENTION

The immune response is coordinated by the actions of cytokines produced from activated T lymphocytes. T lymphocytes having a broad spectrum of antigen receptors are produced in the thymus as a product of the processes of selection and differentiation. When these T cells migrate to the peripheral lymphoid organs and encounter antigen, they undergo activation, during the process of which they produce large numbers of cytokines that act upon other cells of the immune system to coordinate their behavior to bring about an effective immune response.

T lymphocyte activation involves the specific regulation of many genes from minutes after the antigen encounter until at least 10 days later. T cells may also be activated by stimuli such as the combination of a calcium ionophore (e.g., ionomycin) and an activator of protein kinase C, such as phorbol myristate acetate (PMA). Several lectins, including phytohemagglutinin (PHA) may also be used to activate T cells (Nowell, P. C. (1990) Cancer Res. 20:462–466). The T cell activation genes are roughly grouped based on the time after stimulation at which each gene is regulated. Early genes trigger the regulation of subsequent genes in the activation pathway.

Because of the critical role of the T lymphocyte, agents that interfere with the early activation genes, such as cyclosporin A and FK506, are effective immunosuppressants. These early activation genes are regulated by transcription factors, such as NF-AT, that in turn are regulated through interactions with the antigen receptor. These transcription factors act through enhancer and promoter elements on the early activation genes to modulate their rate of transcription.

A typical early gene enhancer element is located in the first 325 base pairs upstream of the start site of the interleukin-2 gene. This region has been used extensively to dissect the requirements for T lymphocyte activation. This region binds an array of transcription factors including NF-AT, NFkB, AP-1, Oct-1, and a newly identified protein that associates with Oct-1 called OAP-40. These different transcription factors act together to integrate the complex requirements for T lymphocyte activation.

NF-AT appears to be the most important element among the group mentioned above in that it is able to direct transcription of any genes to activated T cells in the context of an intact transgenic animal (Verweij et al. J. Biol. Chem. 265:15788–15795 1990). NF-AT is also the only element that requires physiologic activation through the antigen receptor for the activation of transcription by NF-AT. For example, the element is activated only after proper presentation of antigen of exactly the correct sequence by MHC-matched antigen presenting cells. This effect can be mimicked by pharmacologic agents, including the combination of ionomycin and PMA, which can also activate T cells through critical early genes.

Other elements within the IL-2 enhancer, for example, the NFkB site or the AP-1 site, activate transcription in response to less specific stimuli, such as tumor necrosis factor α or simply PMA by itself. These compounds do not activate the IL-2 gene and other early activation genes and do not lead to T cell activation. Such observations have led to the conclusion that NF-AT restricts the expression of certain early genes, such as the interleukin-2 gene to their proper biologic context. Preliminary data have also indicated that a selective genetic deficiency of NF-AT produces severe combined immunodeficiency (SCID) (Chatilla, T. et al. New Engl. J. Med. 320:696–702 1989).

As noted above, cyclosporin A (CsA) and FK506 are capable of acting as immunosuppressants. These agents inhibit T and B cell activation, mast cell degranulation and other processes essential to an effective immune response (ref. 1–3). In T lymphocytes, these drugs disrupt an unknown step in the transmission of signals from the T cell antigen receptor to cytokine genes that coordinate the immune response (ref. 4–6).

Putative intracellular receptors for FK506 and CsA have been described and found to be cistrans prolyl isomerases (ref. 7–11). Binding of the drugs inhibits isomerase activity (ref. 8,10,11); however, studies with other prolyl isomerase inhibitors (ref. 12) and analysis of cyclosporin-resistant mutants in yeast suggest that the relevant biologic activity is an inhibitory complex formed between the drug and isomerase (ref. 13,14) and not isomerase activity per se.

The transcription factor NF-AT appears to be a specific target of cyclosporin A and FK506, since transcription directed by this protein is completely blocked in T cells treated with these drugs, with little or no effect on other transcription factors, such as AP-1 and NF-κB (ref. 15–17). However, the drugs' actual mechanism of action remains unclear. Unfortunately, while both are potent immunosuppressive agents, neither cyclosporin nor FK506 are ideal drugs.

For example, cyclosporin adverse reactions include renal dysfunction, tremors, nausea and hypertension. Indeed, for many years researchers have attempted to develop superior replacements, with FK506 being the most recent candidate. Without understanding how cyclosporin (or FK506) functions at the intracellular level, developing improved immunosuppressants represents an extremely difficult research effort with a very limited likelihood of success.

Thus, there exists a significant need to understand the functional basis of cyclosporin and FK506 effectiveness. With such knowledge, improved assays for screening drug candidates would become feasible, which could in turn dramatically enhance the search process. The present invention fulfills these and other needs.

SUMMARY OF THE INVENTION

The present invention provides novel methods and compositions useful in screening for immunosuppressive agents. The invention is based in part on the discovery of the overall mechanism by which NF-AT is formed intracellularly from nuclear and cytoplasmic subunits.

In accordance with one aspect of the invention, novel compositions include an NF-AT$_c$ polypeptide, an NF-AT$_c$ polypeptide, mixtures of the polypeptides, and cellular extracts containing the polypeptides. The NF-AT$_n$ and NF-AT$_c$ subunits are capable of forming a native NF-AT complex which binds in a sequence-specific manner to a transcriptional regulatory DNA sequence of an immune response gene. The NF-AT$_n$ subunit is characterized by:

i. a molecular weight of about 45 kd;

ii. inducible expression in T cells (such as Jurkat cells);

iii. inducible expression in HeLa cells by exposing the cells to an agent (such as PMA) capable of activating protein kinase C;

iv. a lack of effect by cyclosporin and FK506 on NF-$AT_n$ synthesis in T cells; and v. specifically binding to an NF-$AT_c$.

The NF-$AT_c$ subunit is characterized by:

i. a molecular weight of about 90 kd;

ii. constitutively expressed in T cells;

iii. ability to be transported into a nucleus after a $Ca^{++}$ flux in the cell;

iv. nuclear transport inhibited by cyclosporin and FK506; and v. specifically binding to an NF-$AT_n$.

In another aspect of the present invention, isolated or purified nucleic acid sequences (or their complementary sequences) are provided which are capable of binding to an NF-AT complex, wherein the sequences are substantially homologous to an enhancer, such as IL-2 and IL-4 enhancers, particularly the sequence AAGAGGAAAAA (SEQ. ID NO:1).

In another aspect, the invention embraces methods of screening for an immune regulating agent comprising combining the agent with a component selected from the group consisting of an NF-$AT_n$ polypeptide, an NF-$AT_c$ polypeptide, and mixtures thereof; and determining whether the agent binds to the selected component.

In general, methods of screening for an immune regulating agent will comprise the steps of:

i. preparing a collection of eukaroytic cells containing NF-$AT_c$ in cytoplasm of the cell;

ii. treating the cells with a putative agent;

iii. assaying for nuclear translocation of the NF-$AT_c$ wherein blocking of nuclear transport correlates with the immunosuppressive activity of the agent. The step of assaying for nuclear translocation preferably comprises determining the nuclear presence of the NF-$AT_c$ which is labelled with a detectable marker. Alternatively, the step of assaying for nuclear translocation comprises determining nuclear association between the NF-$AT_c$ and an NF-$AT_n$, preferably using nuclei treated previously with the agent.

The assaying step can also comprise determining binding of NF-AT to a DNA sequence in the cell, such as by determining mNRA transcription levels in the cell, wherein the mRNA encodes an immune response gene.

In a different embodiment, the method of screening for immune regulating agents can comprise:

i. constructing a chimeric gene comprising an NF-AT regulated enhancer region linked to a test gene;

ii. inserting the chimeric gene into T cells;

iii. treating the T cells with T cell activating compounds in the presence or absence of the agent; and iv. determining the effect of the agent on expression of the test gene. Expression of the test gene can inhibit T cell proliferation or causes cell death. Otherwise, where the test gene expression product can be essential for T cell proliferation or for cell viability.

In yet another embodiment, methods of assaying for a putative immunosuppressant agent comprise mixing the agent with NF-$AT_n$ and NF-$AT_c$ under conditions which permit specific dimerization to form NF-AT between the NF-$AT_n$ and NF-$AT_c$, and determining whether the dimerization occurs. Typically, NF-$AT_n$ or NF-$AT_c$ is immobilized and at least one subunit is labelled with a detectable marker.

BRIEF DESCRIPTION OF THE FIGURES

FIGS. 6a–6d. NF-AT binding activity can be quantitatively reconstituted from nuclear and cytoplasmic fractions of stimulated/FK506- and stimulated/CsA-treated Jurkat cells. (a) In lanes 1–6, nuclear extracts (10 μg) and cytoplasmic extracts (10 μg) from nonstimulated (ns), stimulated (s) with PMA/ionomycin, and stimulated/FK506-treated (s+F) cells were tested for NF-AT binding activity using electrophoretic gel mobility shift assays. In lanes 7–10, NF-AT was reconstituted by mixing nuclear and cytoplasmic extracts. Stimulated/FK506-treated (s+F) nuclear extracts (5 μg) were complemented with cytoplasmic extracts (5 μg) from: lane 7, nonstimulated (ns); lane 8, stimulated (s); lane 9, stimulated/FK506-treated (s+F); and lane 10, stimulated/ rapamycin-treated (rap) cells. In all cases arrows indicate the NF-AT protein DNA complex. (b) In lanes 1–3, mixing of nuclear extracts from nonstimulated cells (5 μg) with any cytoplasmic extracts (5 μg) fails to reconstitute NF-AT binding. In lanes 4–9, reconstituted NF-AT binding activity-demonstrates DNA binding specificity: nuclear extracts (5 μg) from stimulated/FK506-treated cells (s+F) were mixed with cytoplasmic extracts (5 μg) and competition was carried out with 10 ng of unlabeled NF-AT or mutant NF-AT oligonucleotide. (c) The effect of FK506 was tested on a murine T cell hybridoma, JK12/90.1 (ref. 23). In lanes 1–3, nuclear extracts (10 μg) from nonstimulated/FK506-treated (s+F) Jurkat cells were tested for NF-AT binding activity. Lane 6 shows NF-AT binding in nuclear extracts from stimulated/FK506-treated (s+F) JK12/90.1 cells. In lanes 4–5 and 7–8, NF-AT is reconstituted by mixing nuclear extracts (5 μg) from stimulated/FK506-treated Jurkat or JK12/90.1 cells with cytoplasmic extracts (5 μg) from non-stimulated Jurkat or JK12/90.1 cells. (d) In lanes 1–3, nuclear extracts (5 μg) from nonstimulated (ns), stimulated (s), and stimulated/cyclosporin A-treated (s+C) cells. Stimulated/cyclosporin A-treated (s+C) nuclear extracts (5 μg) were complemented with cytoplasmic fractions (5 μg) from: lane 4, nonstimulated (ns); lane 5, stimulated (s); and lane 6, stimulated/cyclosporin A-treated (s+C) cells.

DESCRIPTION OF THE PREFERRED EMBODIMENT

Figure 1:
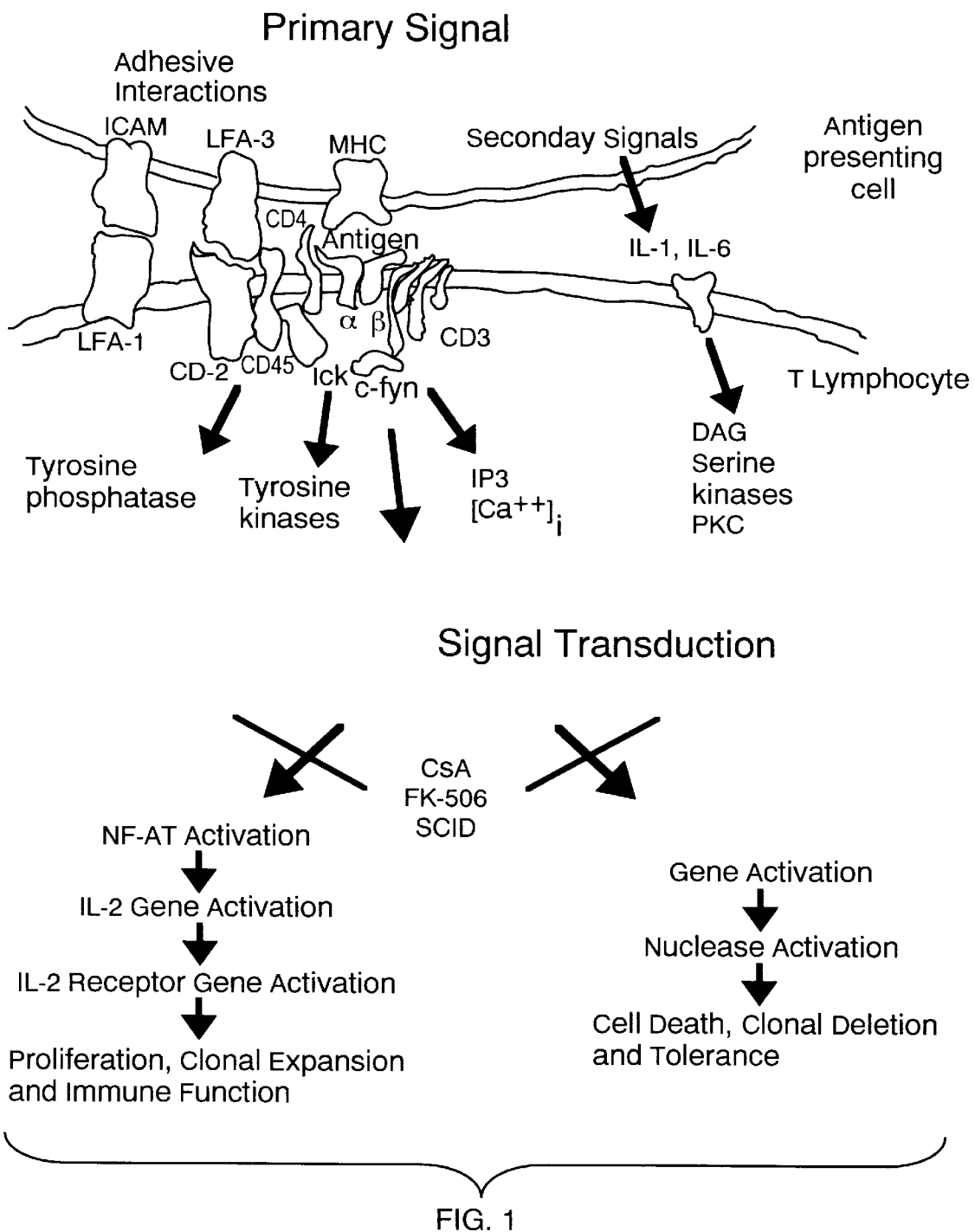
FIG. 1. Representation of the signal transmission pathways carrying information from the T lymphocyte antigen receptor to the early activation genes that lead to proliferation, clonal expansion and immune function or to cell death (apoptosis), clonal deletion and tolerance. Primary signals emanate from the interaction of the T cell antigen receptor (includes the TCR and CD3 complex) with antigen bound by the major histocompatibility complex (MHC). Accessory signalling molecules such as CD2, CD4, and LFA-1 augment the primary signal. A secondary signal that is required to completely activate T lymphocytes is provided by interleukins 1 and 6. These initial signals are transmitted to the nucleus by second messengers such as tyrosine phosphatases (CD-45), tyrosine kinases (lck and fyn), as well as by protein kinase C (PKC) and intracellular calcium. As depicted in the schematic, immunosuppressive drugs such as FK506 and cyclosporin (CsA) as well as immune deficiency diseases (SCID) interfere with the proper transmission of signals from the TCR to the nucleus.

The present invention pertains to means of modulating transcription dependent upon the NF-AT site as well as methods of causing and preventing activation of the factor, controlling expression of the early T lymphocyte activation genes, and controlling transcription of the human immunodeficiency virus. The invention also relates to the formation of active NF-AT from nuclear and cytoplasmic subunits by a novel mechanism; control of induction of the nuclear precursor of NF-AT, as well as control of the nuclear import of the cytoplasmic precursor of NF-AT, methods by which the nuclear import of NF-AT can be modulated and methods by which the induction of the nuclear subunit of NF-AT can be prevented or enhanced. The methods of this invention are useful in determining or controlling the expression of early T lymphocyte activation genes as well as determining or controlling the expression of selected constitutive genes that can be advantageously expressed in T lymphocytes. In addition, the invention also pertains to the development of screening assays for agents that modulate the nuclear import of the cytoplasmic subunit of NF-AT or the induction of the nuclear subunit of NF-AT.

A distinguishing feature of the NF-AT DNA binding site is its purine-rich binding site 5'-AAGAGGAAAAA-3' (SEQ. ID NO:2). DNA sequence comparisons of the promoter/enhancer regions of several genes that respond to T-cell activation signals has identified putative NF-AT protein binding sites. Such a comparison suggests that NF-AT or a related family member may bind within the promoter/enhancer regions of other T-cell activation dependent genes. Most of these genes are sensitive to immunosuppressants, such as FK506 and cyclosporin. A list of putative NF-AT binding sites follows in Table I:

TABLE I

| Purine Rich Core Sequences | Position | Gene |
| --- | --- | --- |
| GAAAGGAGGAAAAACTGTTT (SEQ ID NO:3) | (−289 to −270) | human IL-2 |
| CCAAAGAGGAAAATTTGTTT (SEQ ID NO:4) | (−293 to −274) | murine IL-2 |
| CAGAAGAGGAAAAATGAAGG (SEQ ID NO:5) | (−143 to −124) | human IL-2 |
| TCCAGGAGAAAAAATGCCTC (SEQ ID NO:6) | (−143 to −124) | human IL-4 |
| AAAACTTGIGAAAATACGTA (SEQ ID NO:7) | (−71 to −52) | human g-IFN |
| TAAAGGAGAGAACACCAGCT (SEQ ID NO:8) | (−270 to −251) | HIV-LTR |
| GCAGGGTGGGAAAGGCCTTT (SEQ ID NO:9) | (−241 to −222) | murine GM-CSF |

(Abbreviations: IL-2, interleukin 2; IL-4, interleukin 4; HIV-LTR, human immunodeficiency virus long terminal repeat; GM-CSF, granulocyte-macrophage colony stimulating factor.)

Other NF-AT specific nucleic acid binding sites, usually at least about 10–150 nucleotides (which may be part of a much longer sequence) substantially homologous to these sequences, particularly the NF-AT DNA binding site of the IL-2 enhancer. Ordinarily, such sequences will be about 80% homologous to the NF-AT DNA binding site, preferably in excess of 90% homologous or more.

Methods for screening compounds that prevent the NF-ATc component from translocating to the nucleus are preferably based on the observation that immunosuppressants, such as FK506 and CsA, inhibit NF-ATc from entering the nucleus of FK506 and CsA treated T-cells. This inhibition may occur by modifying the NF-ATc component so that NF-ATc is unable to engage in entry to the nucleus. Thus, an assay typically involves identifying the peptide region of NF-ATc that modification occurs and then using this peptide and/or modification to screen compounds which inhibit or enhance this modification of NF-ATc, all in accordance with standard procedures.

Alternatively, the nuclear pore of the T-cell may be altered to prevent entry of NFATc into the nucleus. Such an assay involves analyzing translocation of NF-ATc or a corresponding peptide into nuclei that had been previously treated with compounds which alter the nuclear pore of the T-cell so that NF-ATc translocation through or association with the nuclear pore structure fails to occur.

These methods of screening may involve labelling NF-ATc or corresponding peptide with any of a myriad of suitable markers, including radiolabels (e.g., $^{125}$I or $^{32}$P), various fluorescent labels and enzymes, (e.g., glutathione-S-transferase and β-galactosidase). If desired for basic binding assays, one of the components may be immobilized by standard techniques.

The screening assays of the present invention may utilize isolated or purified forms of these assay components. This refers to nucleic acid segments, polypeptides and the like of the present invention which have been separated from their native environment (e.g., a cytoplasmic or nuclear fraction of a cell), to at least about 10–50% purity. A substantially pure composition includes such compounds that are approaching homogeneity, i.e., about 80–90% pure, preferably 95–99% pure.

While any of the standard pharmaceutical sources of therapeutic candidate agents may be used, a preferred class of agents suitable for use in the screening assays of the present invention are macrolides, particularly those exhibiting a twisted amide peptidyl prolyl bond. See, Schrieber, Science, 251, 283–287 (1991) and Banerji et al., Mol. and Cell. Biol., 11, 4074–4087 (1991). These compounds are also preferably capable of binding to and blocking the cystolic receptors FKBP-12 and FKBP-13. See, Jin et al., Proc. Natl. Acad. Sci., U.S.A., 88, 6671–6681 (1991).

Agent screening using the methods of the present invention can be followed by biological testing to determine if the compound has the desired activities in vitro and in vivo. The ultimate therapeutic agent may be administered directly to the host to be treated or depending on the size of the compounds. Therapeutic formulations may be administered in any conventional dosage formulation. While for the active ingredient may be administered alone, preferably, it is presented as a pharmaceutical formulation. Formulations comprise at least one active ingredient as defined above together with one or more pharmaceutically acceptable carriers thereof. Each carrier must be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration of a therapeutically effective dose. The formulations may conveniently be presented in unit dosage form and may be prepared by any methods well known in the art of pharmacy.

The Role of NF-AT in T Cell Activation

Induction of cytokines in T lymphocytes by specific contact with antigens serves to coordinate the immune response. Cytokines are responsible for the control of proliferation and cell fate decisions among precursors of B cells, granulocytes and macrophages.

The interleukin-2 gene is essential for both the proliferation and immunologic activation of T cells. The signalling pathways which connect the IL-2 gene and a representative and important early gene with the antigen receptor on the T cell surface and the signal transmission pathways between them are illustrated in FIG. 1. The binding site for the NF-AT protein appears to restrict expression of the interleukin-2 gene and other early activation genes to the context of an activated T lymphocyte. This information is based upon past work by Durand et al., Mol. and Cell. Biol. (1988), Shaw et al., Science, (1988), and Verwiej et al., (1990) J. Biol. Chem, 265: 15788–15795 (1990)). Elimination of the NF-AT site from the IL-2 enhancer drastically reduces the ability of the enhancer to function. In addition, arrays of the binding site for the NF-AT protein will direct expression of NF-AT to a specific biologic circumstance, notably the activated T lymphocyte.

Figure 2:
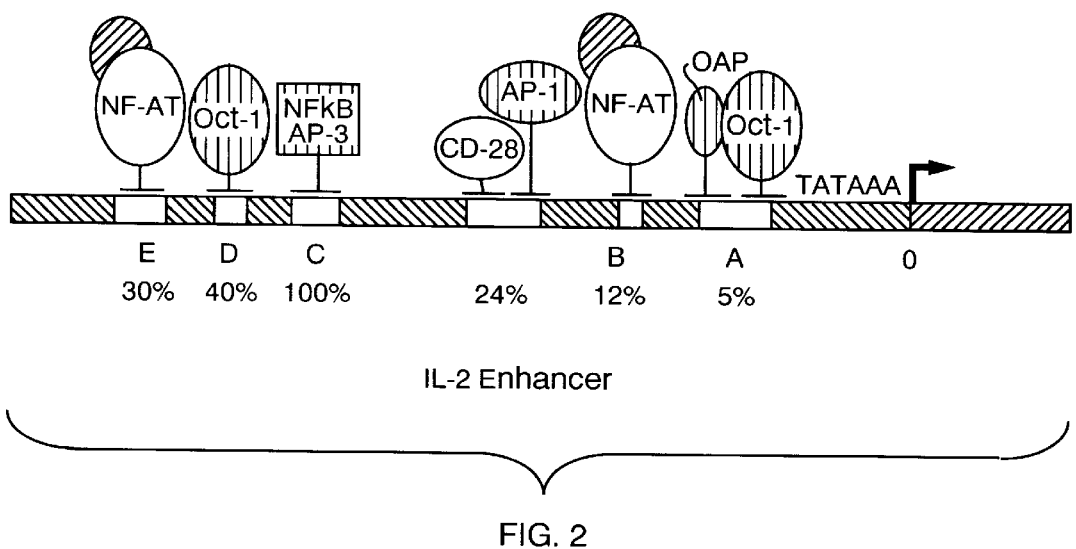
FIG. 2 Diagram of the human IL-2 enhancer from −326 to +47 base pairs. DNase I protected regions are noted by boxes along with the identification of the sites (A–E) and the name(s) of proteins which complex with these sites. Mutations introduced in the boxed regions drastically reduce IL-2 transcription following T lymphocyte activation and are indicated as percent wild type (full) expression remaining. The arrow identifies the transcriptional start site.
Figure 3:
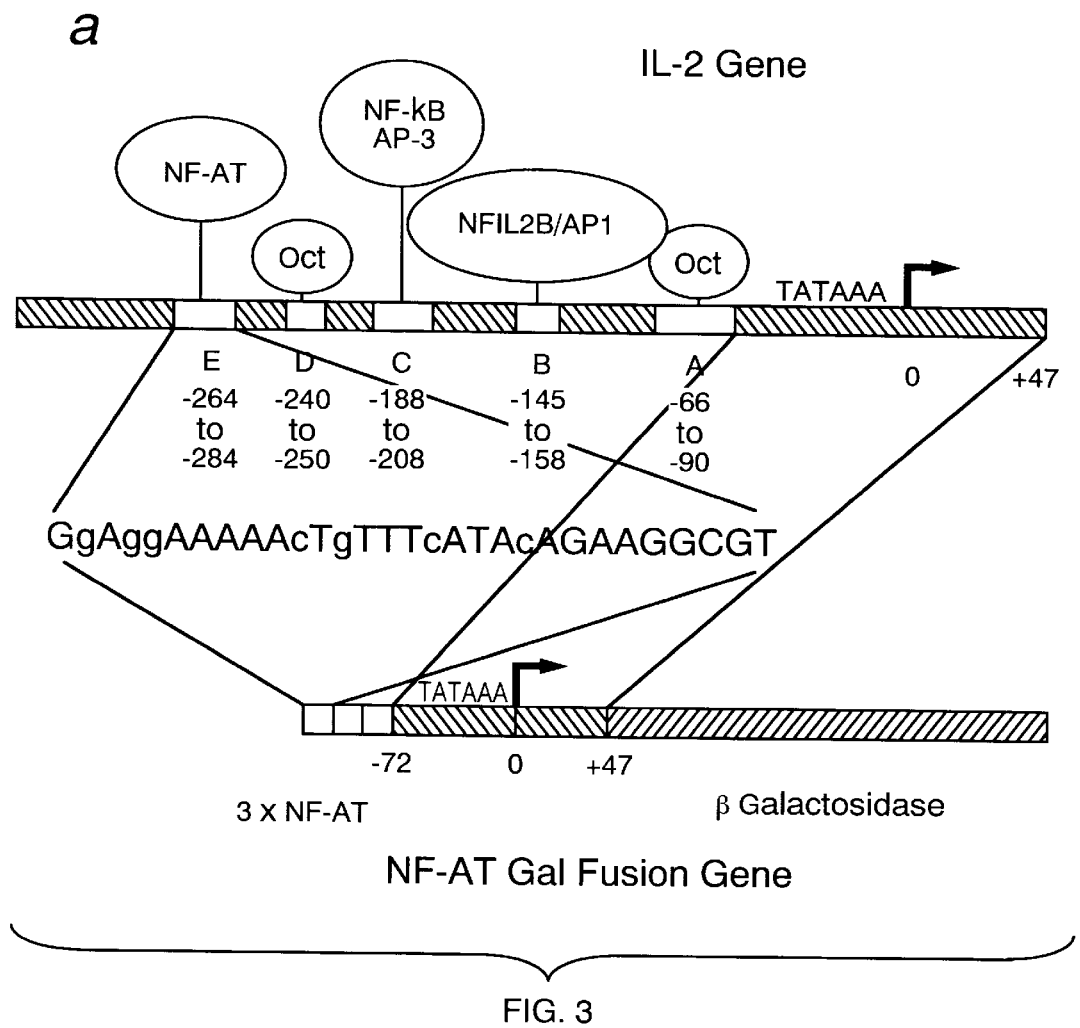
FIG. 3. The diagram shows the NF-AT binding site from the distal element in the interleukin-2 gene. Contact guanine residues are indicated by lower case letters and the construction of binding sites used to measure NF-AT dependent transcriptional activity are shown as an array of three NF-AT binding sites.

Within the interleukin-2 enhancer (FIG. 2), there are two NF-AT sites, a proximal and distal NF-AT site. The sequence of these is shown in detail in FIG. 3 (SEQ ID NO: 19). The essential residues judged by methylation interference are indicated by the lower case letters.

A basis of the present invention is the discovery that NF-AT is formed when a signal from the antigen receptor induces a pre-existing cytoplasmic subunit to translocate to the nucleus and combine with a nuclear subunit of NF-AT. Cyclosporin A and FK506 block translocation of the cytoplasmic component without affecting the nuclear subunit. A plausible synthesis of these studies and previous work posits that the prolyl isomerases, FK506-binding protein (FK-BP) and cyclophilin, also function to import proteins to the nucleus.

The broad scope of this invention is best understood with reference to the following examples, which are not intended to limit the inventions in any manner.

EXAMPLE I

NF-AT is Enriched in Activated T Cells

A DNA binding assay was used to determine the amount of NF-AT present in nuclear extracts from several stimulated and unstimulated cell lines. A radiolabelled oligonucleotide probe corresponding to the NF-AT binding site was hybridized to concentrated nuclear extracts to determine the amount of NF-AT DNA binding activity present.

PROCEDURE

Nuclear extracts were made according to the procedures of Ohlsson and Edlund (Cell 45:35 (1986)) Briefly, nuclei were extracted with 0.3M $(NH_4)_2SO_4$ and the fraction that contained the nuclear proteins was precipitated with 0.2 g/ml $(NH_4)_2SO_4$ and dialyzed for 4 h. at 4° C. The NF-AT binding site of the IL-2 enhancer (−290 and −263) was used as a probe for binding activity. The binding experiment was carried out essentially as described in Shaw, J. P. *Science* 241:202–205 (1988)).

RESULTS

Figure 4:
FIG. 4. NF-AT is T-cell enriched and is formed following activation of T lymphocytes. Representation of NF-AT in different cell lines. Nuclear extracts from: J, Jurkat cells; K, KB cells (a derivative of HeLa cells); F, Faza cells (a rat liver cell line); H, Hep G2 cells (a human hepatocyte line); T, TEPC murine B-cell line; E, EL-4 murine T-cell line; C, C2C12 murine myoblasts. Lanes labelled "+" are the complexes formed with nuclear extracts from cells treated with PHA (2 ug/ml) and PMA (50 ng/ml) for two hours.
Figure 4:
Figure 4:
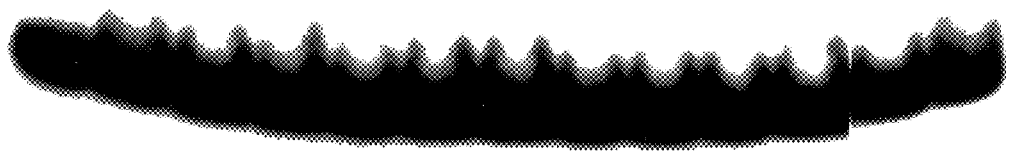

As shown in FIG. 4, using a simple gel mobility shift assay, a complex forms with the NF-AT DNA-binding sequence and proteins present in nuclear extracts of activated T cells but not with extracts of non-activated T cells or other types of cells. Only the nuclear extract from the Jurkat T cell line that had been stimulated with the T cell activating agents PMA and PHA contained detectable amounts of NF-AT-specific DNA binding activity.

EXAMPLE II

Protein Synthesis is Required for Production of the Nuclear Component of the NF-AT Complex, While the Cytoplasmic Component is Preexisting To determine whether protein synthesis is required for formation of the nuclear and cytoplasmic components of the NF-AT complex, or whether the proteins are constitutively present in the cells, an NF-AT-specific DNA binding assay was done using NF-AT complex that had been reconstituted from nuclear and cytoplasmic extracts from cells that had been activated in the presence or absence of a protein synthesis inhibitor.

PROCEDURE

NFATZ Jurkat cells were pretreated with 100 µM anisoymycin (Sigma), a protein synthesis inhibitor, for 30 minutes before stimulating the cells. Conditions for activating the cells and preparing nuclear and cytoplasmic extracts are described in Example III.

RESULTS

Figure 5:
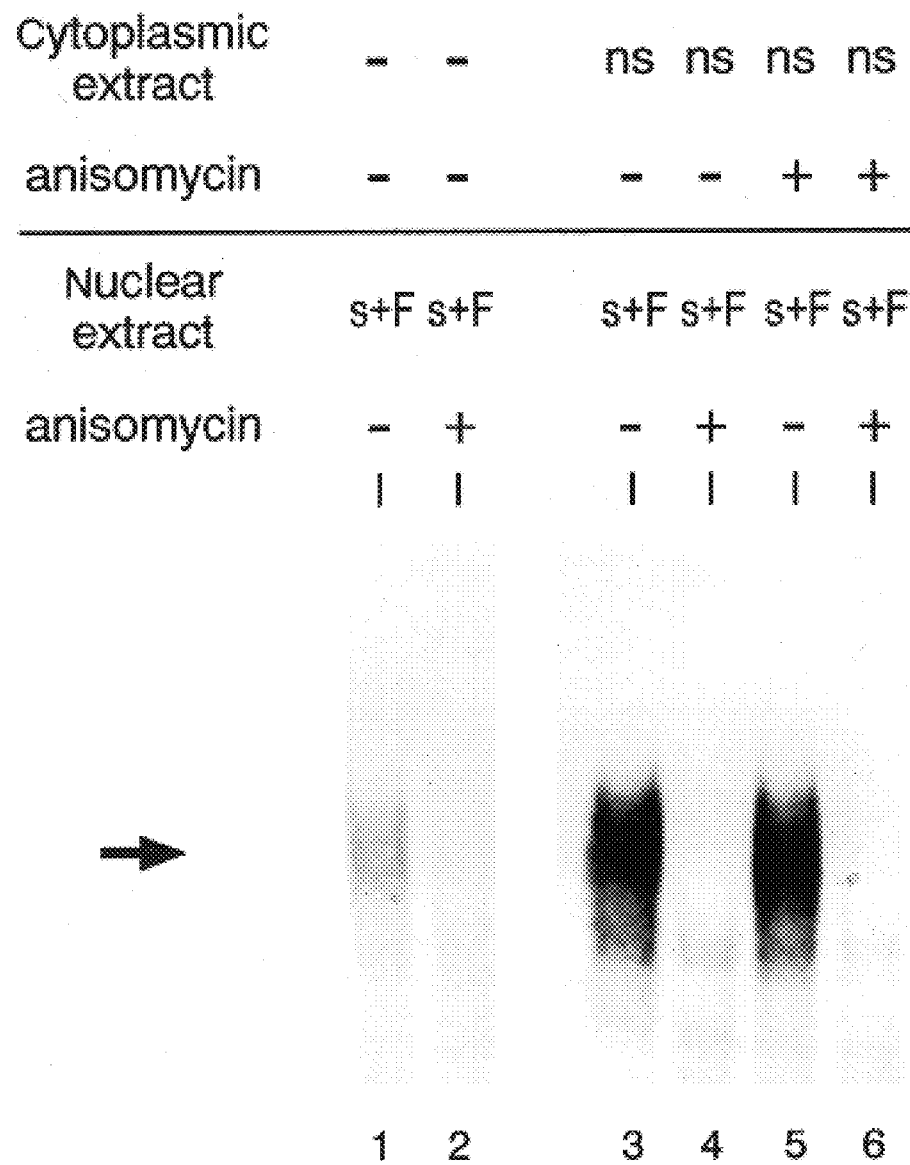
FIG. 5. The nuclear component of the NF-AT complex requires protein synthesis while the cytoplasmic component of NF-AT is pre-existing in T cells. Lanes 1 and 2, gel mobility shift assay using nuclear extracts (10 μg) from stimulated/FK506-treated (s+F) cells in the presence (+) and absence (−) of 100 μM anisomycin. Lanes 3–6, complementation of nuclear extracts from stimulated/FK506-treated cells (with or without anisomycin pretreatment) with cytoplasmic extracts prepared from nonstimulated cells treated with or without anisomycin. Arrows indicate the mobility of the reconstituted NF-AT DNA binding complex.

As shown in FIG. 5, the protein synthesis inhibitor completely blocked the appearance of the NF-AT complex in activated T cells (Lanes 2,4,6). This demonstrates that the nuclear component of the NF-AT complex is made de novo upon activation of the T cells. In contrast, cytoplasmic extracts prepared from cells grown in the presence or absence of a protein synthesis inhibitor were able to reconstitute the NF-AT complex (Lanes 3–6). Thus, the cytoplasmic component of the NF-AT complex is preexisting in the cells prior to stimulation, and additional de novo protein synthesis is not required.

Since the activation of the interleukin-2 gene as well as most early T cell activation genes also requires protein synthesis, these observations are consistent with a prominant role for NF-AT in early gene activation.

EXAMPLE III

NF-AT Can Be Reconstituted From Cytosolic and Nuclear Subunits

A possible interpretation of the data presented in FIG. 5 is that NF-AT is synthesized but sequestered or compartmentalized within the cell and upon breakage of the cells some transcriptionally active NF-AT is formed. To test this hypothesis, the DNA binding ability of NF-AT complexes reconstituted from cytosolic and nuclear extracts from stimulated and non-stimulated T cells, as well as from cells that had been treated with FK506 just prior to stimulation was tested.

PROCEDURE

NFATZ Jurkat cells and JK12/90.1 cells (a gift from N. Shastri) were stimulated for 2 hours with 20 ng/ml PMA and 2 µM ionomycin. To quantitatively-block NF-AT formation, FK506 100 ng/ml or CsA (Sandoz) 500 ng/ml were used five minutes prior to the addition of PMA and ionomycin, without any toxic effects to the cells. Nuclear extracts were prepared as described previously with modifications. Cytoplasmic extracts were made from the same cells as the nuclear extracts. Following lysis of the cells with buffer A [10 mM Hepes (pH 7.8), 15 mM CKl, 2 mM $MgCl_2$, 1 mM DTT, 0.1 mM EDTA, 0.1 mM PMSF] plus 0.05% NP-40, and pelleting of the nuclei, the cytoplasmic fraction was removed and stabilized with 10% (vol/vol) glycerol and 1/10 volume of buffer B [0.3M Hepes (pH 7.8), 1.4M KCl, and 30 mM $MgCl_2$]. The cytoplasmic extract was centrifuged at 200,000 g for 15 minutes. An equal volume of 3M $(NH_4)_2SO_4$ (pH 7.9) was added to the supernatant, and precipitated proteins were pelleted at 100,000 g for 10 minutes. The pelleted cytoplasmic proteins were resuspended in buffer C [50 mM Hepes (pH 7.8), 50 mM KCl, 1 mM DTT, 0.1 mM EDTA, 0.1 mM PMSF, 10% (vol/vol) glycerol] and desalted by passage over a P6DG column (BioRad). Protein concentrations were determined using a BioRad protein assay kit. To assess the completeness of the nuclear and cytoplasmic fractionation, we assayed for Oct-1 (a constitutive nuclear located DNA binding protein) binding activity and β-galactosidase (cytoplasmic localized) enzyme activity. We found no Oct-1 binding activity in the cytoplasmic fraction and found that β-galactosidase activity is present in the cytosol at 3.7-fold higher concentration than in the nuclear fraction (data not shown). Electrophoretic mobility shift assays were done essentially as described. Fried, M. and D. M. Crothers NAR 9:6505–6526 (1981). Binding reactions were carried out as previously described. Fiering, S. et al. Genes Dev. 4 1823–1834 (1981). Total amount of protein used in each binding reaction was 10 µg. The end-labelled binding site for NF-AT was derived from the human IL-2 enhancer (−285 to −255 bp). The oligonucleotide sequence is 5'-gatcGGAGGAAAAACTGTTCATACAGAAGGGGT-3' (SEQ. ID NO:10). The mutant NF-AT probe essentially differs from the NF-AT oligonucleotide at four contact guanosine residues. The sequence is 5'-gatcAAGAAAGGAGtAAAAAaTtTTTaATACAGAA-3' (SEQ. ID NO:11). Lower case letters indicate mutated residues. Competition with 10 ng of unlabeled oligonucleotide represents a 100- to 200-fold molar excess over labeled probe.

RESULTS

In the nuclear extracts prepared from stimulated/FK506-treated cells, NF-AT binding activity is reduced substantially and is not observed in the cytoplasmic fractions (FIG. 6a, lanes 3 and 6). Remarkably, binding activity was completely reconstituted by mixing nuclear extracts from stimulated/FK506-treated cells together with cytoplasmic fractions from nonstimulated, or stimulated/FK506-treated cells, neither of which have NF-AT binding activity (FIG. 6a, lanes 7 and 9). Although the mobility of the reconstituted DNA-protein complex is slightly faster than the characteristic mobility of the NF-AT complex, DNA binding specificity is identical (FIG. 6b, lanes 4–9). Nuclear extracts from non-stimulated cells are not complemented by any of the cytoplasmic extracts (FIG. 6b, lanes 1–3) suggesting that stimulation of the cells is essential for synthesis of the nuclear component of NF-AT.

While cytoplasmic extracts from nonstimulated and stimulated/FK506-treated cells can reconstitute the NF-AT complex, cytoplasmic extracts from stimulated cells show only partial reconstitution of NF-AT binding activity (FIG. 6a, lane 8) implying that the cytoplasmic component of NF-AT pre-exists in nonstimulated cytoplasmic extracts and is translocated to the nucleus following stimulation in the absence of FK506.

We used rapamycin as a control for non-specific effects of FK506. Rapamycin is a structural analog of FK506, and like FK506, contains a structural mimic of a twisted leucyl-prolyl amide bond, binds FK-BP, and inhibits its isomerase activity (refs. 12,13,20). Despite the fact that rapamycin inhibits isomerase activity, it antagonizes the actions of FK506 on NF-AT-directed transcription, IL-2 gene activation, T cell activation, and programmed cell death (refs. 13,21,22). Rapamycin did not block translocation of the cytoplasmic component of NF-AT to the nucleus following activation (FIG. 6a, lane 10). This is consistent with its failure to block NF-AT directed transcription (ref. 17).

Figure 6C:
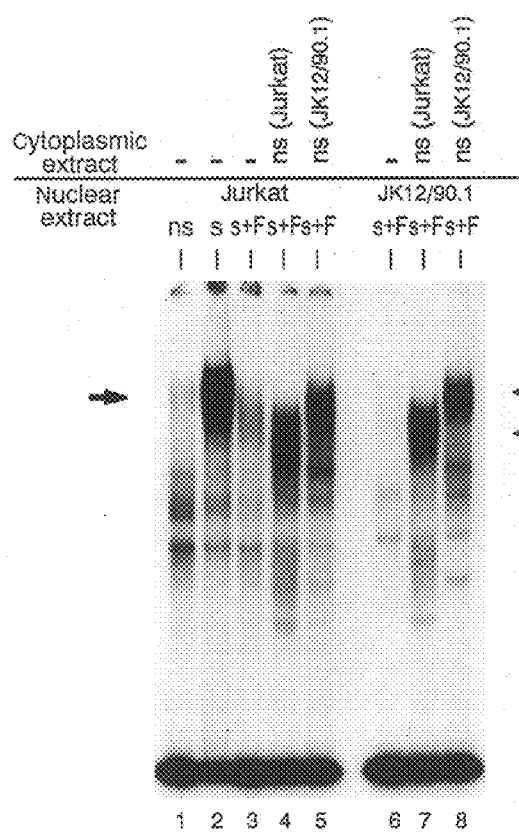

To determine if impaired nuclear import is also a property of the immunosuppressive prolyl isomerase inhibitor CsA, we tested the effects of CsA. The biological effects of FK506 and CsA on the immune response are essentially identical (ref. 23). CsA completely blocks NF-AT directed transcription in T cells and extracts of cells stimulated in the presence of CsA contain less NF-AT binding activity than stimulated controls (ref. 16). Accordingly, mixing nuclear extracts from stimulated CsA-treated cells with cytoplasmic extracts from the same cells or nonstimulated cells reconstitutes NF-AT binding activity (FIG. 6c, lanes 4–6). Again, nonstimulated nuclear extracts are not able to be complemented by any cytoplasmic extract (FIG. 6c, lanes 1–3). Thus, these results suggest that CsA and FK506 both block the translocation of a pre-existing cytoplasmic component which constitutes part of the NF-AT DNA binding complex.

EXAMPLE IV

The Cytosolic Form of NF-AT (NF-AT$_c$) is Selectively Expressed in T Cells

Despite the fact that the actions of CsA and FK506 are tissue specific, their binding proteins are ubiquitous (refs. 27–31). This apparent quandary could be rationalized if the drug-isomerase complex acted on a T cell specific molecule. To determine whether the components of the NF-AT complex are found in cell types other than T cells, we tested whether nuclear or cytoplasmic extracts of HeLa cells can be used to reconstitute NF-At complex alone or in conjunction with extracts from Jurkat cells.

PROCEDURE

Figure 6D:
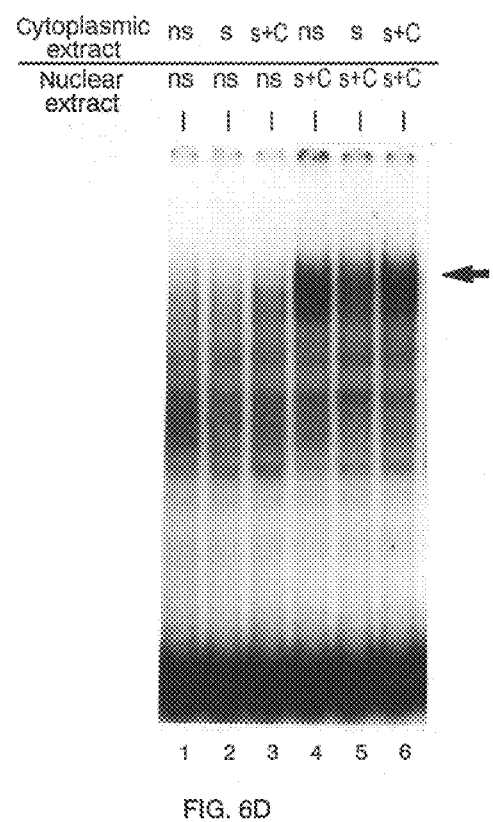

HeLa S3 cells were grown in spinner flasks at 37° C. in S-MEM (Gibco-BRL) supplemented with 5% fetal calf serum, penicillin (100 U/ml), and 100 µg/ml of streptomycin. HeLa S3 were stimulated, nuclear and cytoplasmic extracts were prepared, and gel mobility shift assays were carried out under conditions identical to those described in FIG. 6.

RESULTS

Figure 7A:
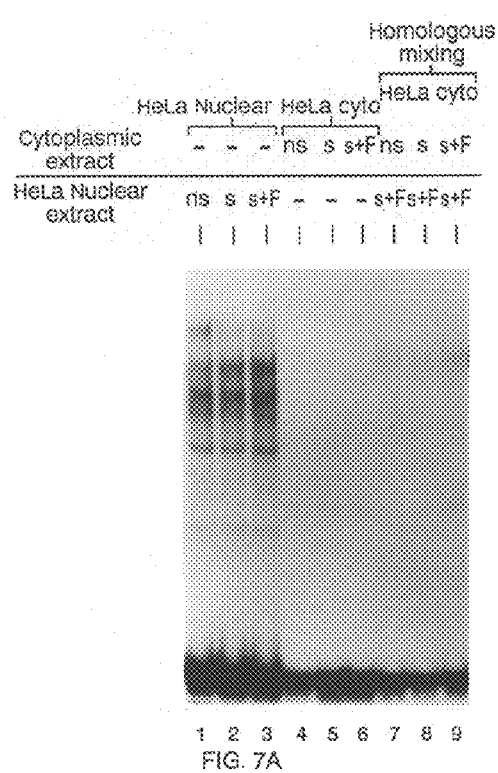
FIGS. 7a–7c. The nuclear component of NF-AT is present in HeLa cells and can be complemented by Jurkat cytoplasm, but not by HeLa cell cytoplasm, to reconstitute NF-AT binding activity. (a) Lanes 1–6, gel mobility shift assay using HeLa nuclear (10 μg) and cytoplasmic (10 μg) extracts from nonstimulated (ns), stimulated (s), and stimulated/FK506-treated (s+F) cells do not form a NF-AT protein-DNA complex. In lanes 7–9, homologous mixing of nuclear extracts (5 μg) from stimulated/FK506-treated (s+F) HeLa cells with HeLa cytoplasmic extracts (5 μg) does not reconstitute NF-AT. (b) NF-AT binding activity is reconstituted with HeLa nuclear and Jurkat cytoplasmic extracts. Nuclear extracts (5 μg) from stimulated/FK506-treated HeLa cells complemented by cytoplasmic extracts (5 μg) from: lane 1, nonstimulated (ns); and lane 3, stimulated/ FK506-treated (s+F) Jurkat cells. In lanes 4–9, reconstituted NF-AT binding complex demonstrates DNA binding specificity when competed by 10 ng of unlabelled NF-AT or mutant NF-AT oligonucleotides. (c) Lanes 1–3, heterologous mixing of Jurkat nuclear extracts (5 μg) from stimulated/FK506-treated (s+F) with HeLa cytoplasmic extracts (5 μg) does not reconstitute NF-AT binding activity.
Figure 7B:
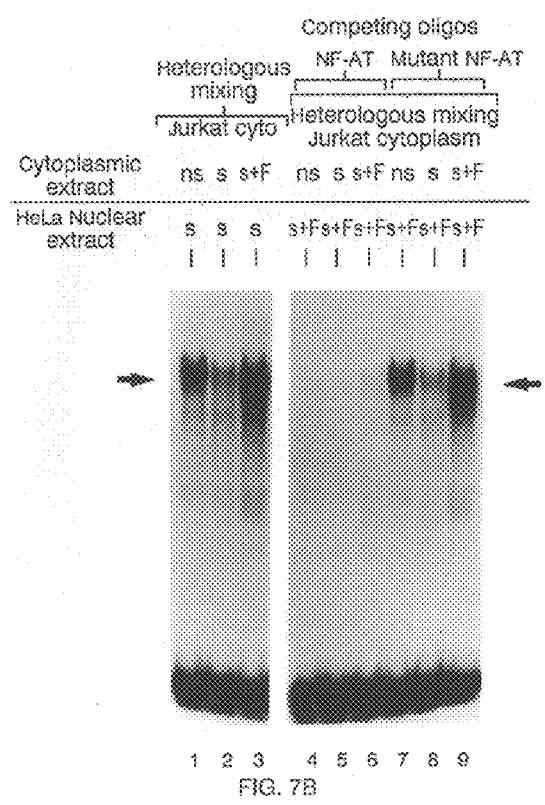
Figure 7C:
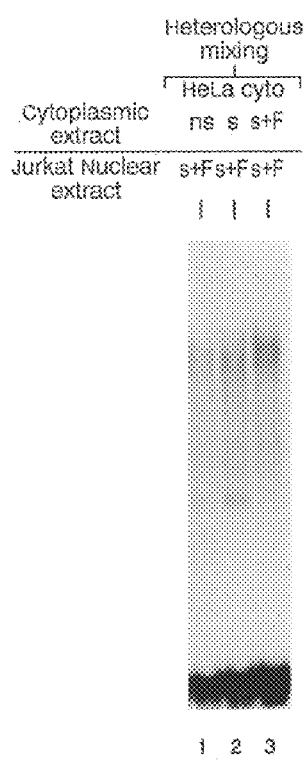

HeLa cytoplasmic extracts do not contain NF-AT and homologous mixing of nuclear and cytoplasmic extracts do not contain NF-AT and homologous mixing of nuclear and cytoplasmic extracts from HeLa cells failed to reconstitute NF-AT binding activity (FIG. 7a, lanes 1–9). In contrast, heterologous mixing of Jurkat cytoplasmic extracts with nuclear extracts from HeLa cells reconstituted NF-AT binding activity (FIG. 7b, lanes 1–3). Furthermore, the reconstituted NF-AT binding activity is specific as demonstrated by oligonucleotide competition (FIG. 7b, lanes 4–9). These results suggest that the oligonucleotide competition (FIG. 7b, lanes 4–9). These results suggest that the nuclear component of NF-AT is present in HeLa cells. In contrast, HeLa cell cytoplasmic extracts cannot reconstitute NF-AT binding activity when mixed with nuclear extracts from stimulated/FK506-treated Jurkat cells (FIG. 7c, lanes 1–3) implying that the cytoplasmic component is T cell specific while the nuclear component of NF-AT is not.

EXAMPLE V

Nuclear Import of the Cytosolic Component Can Be Induced With Ionomycin While Synthesis of the Nuclear Component Requires Only PMA A unifying feature of the actions of FK506 and CsA is that they inhibit processes which require $Ca^{2+}$ mobilization (refs. 17,24–26). Induction of NF-AT binding and transcriptional activity requires physiologic stimuli that are believed to be mimicked by agents that increase intracellular $CA^{2+}$ and activate protein kinase C (PKC)(ref. 15).

To examine the requirements for induction of the nuclear and cytoplasmic subunits of NF-AT, extracts were prepared from cells stimulated with either PMA alone or ionomycin alone and tested for their ability to reconstitute DNA-binding activity.

PROCEDURE

Gel mobility shifts and preparation of nuclear and cytoplasmic extracts were carried out as described in Example III.

RESULTS

Figure 8:
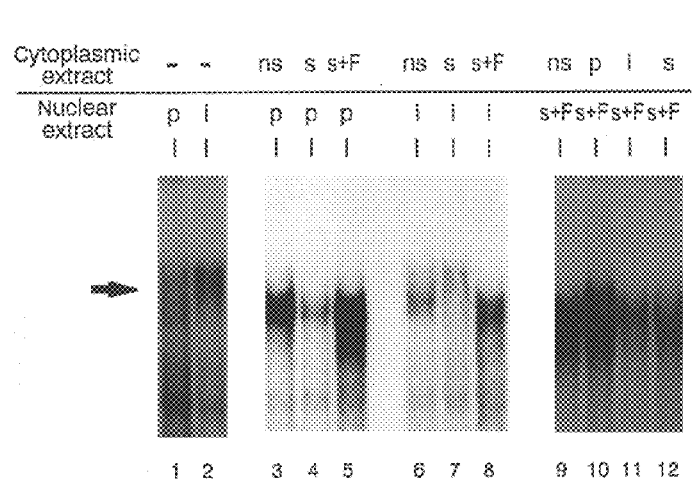
FIG. 8. The nuclear component of NF-AT is induced by PMA while calcium mediated signals allow translocation of the pre-existing cytoplasmic subunit of NF-AT. (a) Lanes 1 and 2, gel mobility shift assay using nuclear extracts (10 μg) from PMA-stimulated (p) and ionomycin-stimulated (i) cells. In lanes 3–8, complementation of nuclear extracts (5 μg) from PMA-stimulated and ionomycin-stimulated cells with cytoplasmic extracts (5 μg) from nonstimulated (ns), stimulated (s), and stimulated/FK506-treated (s+F) cells. Stimulated/FK506-treated (s+F) nuclear extracts (5 μg) were complemented with cytoplasmic extracts (5 μg) from: lane 9, nonstimulated (ns); lane 10, PMA-stimulated (p); lane 11, ionomycin-stimulated (i); and lane 12, stimulated (s) cells. Arrows indicate the NF-AT protein DNA binding complex.

Cytosolic extracts from ionomycin-treated cells show less ability to reconstitute DNA binding when added to nuclear extracts of stimulated FK506-treated cells than either cytosolic extracts from non-stimulated cells, cytosolic extracts from PMA-stimulated cells or cytosolic extracts from cells stimulated with both PMA and ionomycin (FIG. 8). FK506 treatment did not inhibit PMA/ionomycin-stimulated cells from synthesizing the nuclear component of NF-AT (FIG. 8, Lanes 9–12). Furthermore, mixing cytoplasmic extracts from PMA-stimulated or ionomycin-stimulated cells with nuclear extracts from stimulated/FK506-treated cells fail to reconstitute NF-AT DNA-binding activity (FIG. 8, Lanes 4 and 7), suggesting that the pre-existing cytoplasmic subunit translocated to the nucleus. Thus, CsA and FK506 appear to inhibit the $Ca^2$-dependent translocation of the cytoplasmic component of NF-AT.

EXAMPLE VI

FK506 Does Not Inhibit NF-AT-dependent Transcription in vitro

The effect of FK506 on the ability of NF-AT to direct transcription was tested by preparing nuclear extracts from stimulated or stimulated/FK506-treated cells and testing their ability to transcribe a G-less cassette in which transcription was dependent upon three NF-AT sites located within a synthetic promoter.

PROCEDURE

Promoter constructs, nuclear extracts and transcription reactions were prepared as described (WMF and GRC, manuscript submitted). NFATZ Jurkat cells, derived from a human T-cell leukemia, were stimulated with 20 ng/ml PMA (Sigma), 2 µM ionomycin (Calbiochem) for 2 hours. FK506 (gift of S. Schreiber) was used at 10 ng/ml and added five minutes prior to the addition of PMA and ionomycin. Ribonuclease protection assay of the NF-AT/lacZ mRNA was carried out as previously described. Transcription was quantitated using a radioanalytic imaging system (AMBIS).

Using the human Jurkat T cell line[18], we developed an activation-dependent, T cell specific in vitro transcription system which faithfully reflects the complex requirements for IL-2 transcription and more generally T cell activation.

In Vitro Transcription Protocol

PROCEDURE

Cell Culture and Stimulation Conditions

Jurkat cells were grown in RPMI 1640 without L-glutamine, 8% fetal calf serum (FCS) (Irvine Scientific), with penicillin (100 units/ml) and streptomycin sulfate (100 µg/ml) at 5% $CO_2$ concentrations. Cells were split 1:3 thirty-six hours before stimulation. The morning of the stimulation, the Jurkat cells ($1 \times 10^6$ cells/ml) were centrifuged at 3500 rpm (2000×g), in a GS-3 rotor for 10 minutes and then resuspended in fresh media to a concentration of $2 \times 10^6$ cells/ml. In general, 2 µM ionomycin (Calbiochem) and 20 ng/ml PMA (Sigma) were used to stimulate the cells. During the 2 hour stimulation, the cells were constantly shaking to prevent the layering of cells on the bottom of the flask.

Hela S3 cells were grown in S-MEM (Gibco) with 8% GCS, with penicillin (100 units/ml) and streptomycin sulfate (100 µg/ml) and 2 mM L-glutamine. Hela S3 were stimulated with 20 ng/ml PMA and 2 µM ionomycin.

Plasmid Construction

The IL-2 G-less plasmid was constructed by fusing the IL-2 enhancer (−326 to +24) to a 377 base pair (bp) G-less cassette generously provided by R. Roeder (Sawadogo and Roeder, 1985) using polymerase chain reaction overlap extension techniques (Horton, R. M. et al. Gene 77:61–68 1989; Ho, S. N., et al. Gene 77:51–59 1989). The IL-2 enhancer G-less cassette contained on a Xho I-Bam HI fragment was inserted into a pUC derivative containing an Xho I site in the polylinker. To avoid PCR artifacts the entire IL-2 enhancer G-less cassette was sequenced. The total size of the IL-2 enhancer G-less transcript is 401 nucleotides (nt). The NFAT multimer which contains 3 NFAT binding sites (−286 to −257) and NF-IL-2A multimer which contains 4 NF-IL-2A binding sites (−94 to −65) G-less constructs were made by digesting pE3.1 and pA4.1 (Durand et al. 1988) with Asp 718 and Bam HI, respectively, and ligating the fragments into an Asp 718-Bam HI digested τ-fibrinogen G-less cassette construct. τ-fibrinogen G-less was constructed by fusing −54 to +1 of the τ-fibrinogen promoter (Crabtree, G. R. and Kant, J. A. Cell 31:159–166 1982; Durand et al. 1987) to the 377 bp G-less cassette using PCR overlap extension techniques. All regions of the construct made using PCR technology were sequenced to avoid any point mutations using Sequenase DNA sequencing kit (U.S. Biochemical). The τ-fibrinogen promoter is a minimal promoter containing only a Sp1 binding and TATA box. Between +1 of the τ-fibrinogen promoter and the G-less cassette a Ssp I restriction enzyme site was inserted. Both the ARRE-2 and ARRE-1 G-less constructs generate 383 nt transcripts.

The HNF-1 (hepatocyte nuclear factor 1) G-less plasmid was constructed by inserting tandemly linked NF-1 binding sites from Rat β-fibrinogen promoter (−77 to −65) (Courtois et al. 1987) into Xho-Sal polylinker sites in τ-fibrinogen G-less construct. The adenovirus major late promoter (AdMLP) G-less construct was a generous gift of Drs. M. Sawadoga and R. Roeder. Total size of the AdMLP G-less transcript is 280 nt.

Preparation of Nuclear Extracts

Jurkat and liver in vitro transcription nuclear extracts were essentially made as described by Gorski et al. (Gorski et al. 1986; Maire et al. 1989) with some exceptions. First, the cells were broken in 1.5M sucrose-glycerol solution to reduce the amount of frictional heat generated during cell lysis. Second 0.5% (vol/vol) nonfat dry milk was added to the homogenization buffer as had been previously described (Maire et al. 1989). Third, the Jurkat nuclei were fractionated on only one 2.0M sucrose pad preceding salt extraction. Briefly, all manipulations were performed in the cold, and all solutions, tubes, and centrifuges were chilled to 4° C. Protease inhibitors, antipain (1 µg/ml), leupeptin (1 µg/ml), 0.1 mM phenylmethylsulfonyl fluoride (PMSF) and 0.1 mM benzamidine, were added to all buffers except the dialysis buffer. One mM dithiothreitol was added to all buffers. Following stimulation in the case for Jurkats, the cells ($10^9$) were centrifuged in a GS-3 rotor, 3500 rpm (2000×g), for 10 minutes. The media was poured off and the cells were rinsed with 40 mls of phosphate buffered saline. Resuspended pellets were then centrifuged 1000 rpm (200×g), 10 minutes in a Beckman GPR tabletop centrifuge. The cell pellet was resuspended in 10 ml of homogenization buffer (10 mM Hepes [pH 7.6] 25 mM KCl, 0.15 mM spermine, 0.5 mM spermidine, 1 mM EDTA, 1.25M sucrose, 10% glycerol (vol/vol), 0.5% nonfat dry milk (vol/vol). An aqueous 0.1 g/ml nonfat dry milk solution was centrifuged for 10 minutes in a SS-34 rotor at 1000 rpm (11950×g) to remove undissolved milk solids before adding to any solution.

The cells were dounced (Teflon-glass homogenizer) until broken using a ½ hp drill press (Jet Tools Inc) at high speed. Cells were checked for lysis. Generally, greater than 80% of the cells were lysed. Following lysis, 46 mls of 2M sucrose homogenization buffer (10 mM Hepes [pH 7.6], 25 mM KCl, 0.15 mM spermine, 0.5 mM spermidine, 1 mM EDTA, 2M sucrose, 10% glycerol (vol/vol), 0.5% nonfat dry milk (vol/vol) were added to the dounced cells. The homogenized cells (28 mls) were layered on to 10 ml sucrose pads (10 mM Hepes [pH 7.6], 25 mM KCl, 0.15 mM spermine, 0.5 mM spermidine, 1 mM EDTA, 2M sucrose, 10% glycerol (vol/vol) and centrifuged at 24,000 rpm for 60 minutes in a SW 28 rotor (103,000×g).

The pelleted nuclei were resuspended in a total of 6 ml of nuclear lysis buffer (10 mM Hepes [pH 7.6], 100 mM KCl, 3 mM $MgCl_2$, 0.1 mM EDTA, 10% glycerol (vol/vol).) One ninth volume of 3M $(NH_4)_2SO_4$ pH 7.9 was added and mixed constantly for 30 minutes. The viscous lysate was centrifuge 40,000 rpm, 60 minutes, in a Ti 50 rotor (150, 000×g) to pellet the chromatin.

Following centrifugation, the tubes were quickly removed and the supernatant transferred to another tube before the pelleted chromatin began to reswell. To the supernatant, 0.3 grams of solid $(NH_4)_2SO_4$ per ml were added. The tube was gently mixed for 10 minutes or until all the $(NH_4)_2SO_4$ had gone into solution. The tubes were placed on ice for 40 minutes and gently mixed every 10 minutes. The precipitated proteins were then centrifuged for 15–20 minutes, 40,000 rpm, in a Ti 50 rotor (150,000×g). At this point, the pellet was immediately resuspended in dialysis buffer (25 mM Hepes [pH 7.6], 40 mM KCl, 0.1 mM EDTA, 10% glycerol (vol/vol).) Protein extracts from 1×10⁹ Jurkat cells were resuspended in 200–300 μl of dialysis buffer resulting in a final protein concentration of 10 mg/ml. Extracts were dialyzed twice for 2 hours in the cold against 100 volumes of dialysis buffer. During dialysis a precipitate forms that at the end of dialysis was removed by centrifugation in a microfuge (Brinkman Instruments) at a setting of 14 for 5 minutes. Protein concentrations were determined with a Bio-Rad protein assay kit using BSA as a standard. Protein extracts were frozen in small aliquots on dry ice and immediately stored in liquid nitrogen.

HeLa S3 nuclear extracts were made as previously described (Shapiro, D. J. et al. DNA 7:44–45 1988).

Transcription Reactions

In general, transcription reactions (20 μl) contained 40 μg/ml of circular DNA template [400 ng of the test construct, 40 ng of the AdMLP G-less construct, and 360 ng of poly dI-dC (Pharmacia)] and between 3–5 mg/ml nuclear protein extract in a buffer containing 25 mM Hepes (pH 7.6), 50 mM KCl, 6 mM MgCl2, 0.6 mM each of ATP and CTP, 7 μM UTP, 7 μCi [α-$^{32}$P] UTP (Amersham, 400 Ci/mmole), 0.5 mM 3'-O-methyl GTP (Pharmacia), 150 units of RNase T1 (BRL), 12 units of RNase inhibitor (Amersham) and 12% glycerol (vol/vol). EDTA and DTT were contributed by the extract. Transcription reactions using liver or HeLa nuclear extracts contained 40 μg/ml of circular DNA templates (400 ng of the test construct and 400 ng of the AdMLP). All other reaction conditions were kept constant. The reactions were incubated for 45 minutes at 30° C. The transcription reactions were terminated by adding 280 μl of stop buffer (50 mM Tris-HCl [pH 7.6], 1% SDS, 5 mM EDTA) and were extracted two times with phenol and one time with chloroform. The RNA was precipitated with 15 μg of glycogen, 0.3M sodium acetate (pH 5.2) and 2.5 volumes of ETOH. The pellets were rinsed with 70% ethanol, air dried, and resuspended in 10 μl of loading dye (90% formamide, 0.01% xylene cyanol, and 0.01% bromophenol blue in 1×TBE.) The transcripts were analyzed on 6% denaturing polyacrylamide gels. In general, the gels were exposed overnight at room temperature using XAR-5 (Kodak) x-ray film. Normalized fold induction is calculated by normalizing the amount of transcription from the test G-less construct to that observed from the AdMLP G-less construct and then dividing the amount of test G-less transcription from stimulated nuclear extracts by the amount of test G-less transcription from nonstimulated nuclear extracts. Autoradiograms were quantitated using an Ambis radioanalytic imaging system (Ambis Systems, San Diego, Calif.).

RESULTS

Figures 9A, 9B:
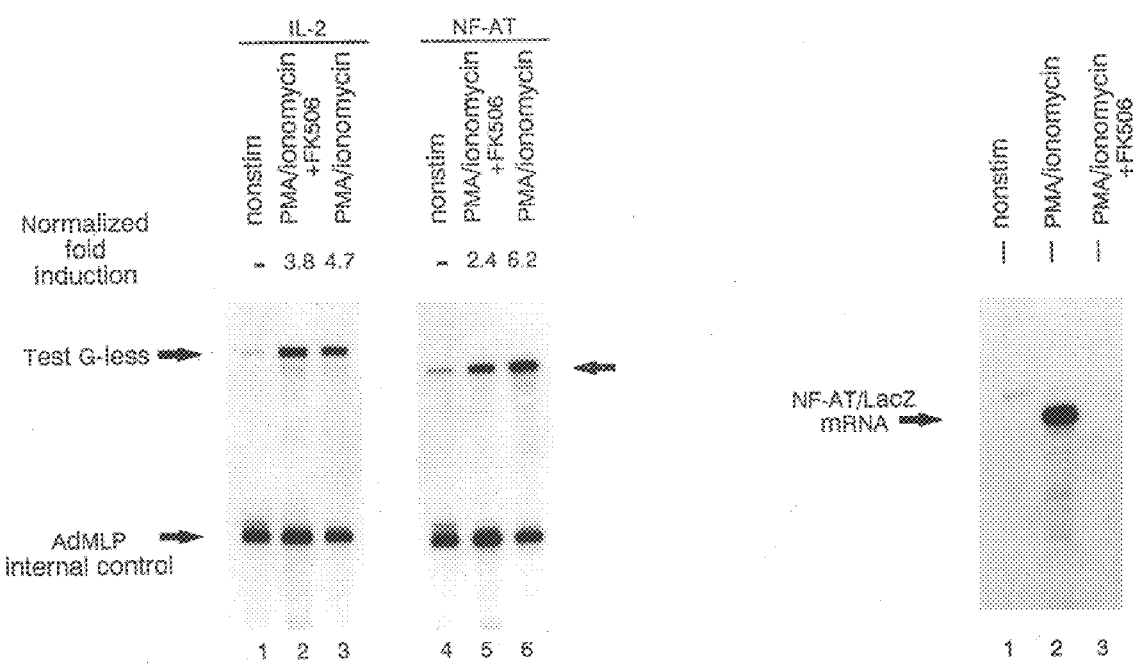
FIGS. 9a–9b. In vitro transcription directed by the IL-2 enhancer or three tandemly linked NF-AT binding sites in nuclear extracts stimulated under different conditions. (a) IL-2 directed transcription: lane 1, nonstimulated; lane 2, PMA/ionomycin/FK506-treated cells; and PMA/ionomycin stimulated cells, lane 3. NF-AT directed transcription: lane 4, cdescriptionde nonstimulated; lane 5, PMA/ionomycin/ FK506-treated cells; lane 6, PMA/ionomycin-stimulated cells. Expression from the IL-2 enhancer and NF-AT G-less template generates a 401 and 383 nucleotide (nt) transcript, respectively. The adenovirus major late promoter (AdMLP) internal control generates a 280 nt transcript. Fold induction is calculated following normalization to AdMLP transcription. (b) Ribonuclease protection assay of NF-AT driven lac Z mRNA. Lane 1, nonstimulated; lane 2, PMA/ionomycin-stimulated; lane 3, PMA/ionomycin/FK506-treated cells.

Surprisingly, nuclear extracts from Jurkat cells that had been stimulated for 2 hours with PMA and ionomycin in the presence of FK506 (10 ng/ml) transcribe the IL-2 G-less template at levels nearly equivalent to extracts from fully stimulated Jurkat cells (FIG. 9a, compare lanes 2 and 3) even though transcription of the endogenous IL-2 gene in these cells is fully inhibited (data not shown). Since most of the inhibitory effects of CsA and FK056 on IL-2 gene activation have been shown to be due to the inhibition of NF-AT function (refs 16,17), we also examined transcription directed by this protein. In vitro transcription directed by multimerized binding sites for the NF-AT protein was reduced 2.5-fold in nuclear extracts of stimulated/FK506-treated cells (FIG. 9a, compare lanes 5 and 6) despite the fact that NF-AT dependent transcription was totally blocked in the cells used to prepare the extracts (FIG. 9b). In these extracts, NF-AT DNA-binding activity is reduced about 50 to 80% far less than the inhibitory effects on in vivo IL-2 gene expression that are generally in excess of 99% (ref. 17), but commensurate with the effects on NF-AT dependent in vitro transcription. Thus, it appears that stimulated/FK506-treated cells contain a reduced amount of NF-AT that functions in vitro but not in vivo.

EXAMPLE VII

Tandem NF-AT Binding Sites Direct Expression of T Antigen to Activated Lymphocytes in Transgenic Mice To determine whether a transcriptional promoter under the control of NF-AT regulatory sites will specifically direct expression of a linked gene to activated lymphocytes, we utilized a cell line that contains a construct in which tandem NF-AT binding sites are linked upstream of a gene encoding T antigen (Verweij et al. J. Biol. Chem. 265: 15788–15795).

PROCEDURE

Total RNA was isolated from various tissues and cells using guandinium thiocyanate and hot phenol extraction. Equal amounts 10 ug of RNA were used. RNA mapping experiments with the Sp6/T7 RNA polymerase system were done according to (Melton, D. A. NAR 12:7035–7056 (1984)). For mapping correctly initiated NF-AT-Tag mRNA, a SP6 RNA probe was transcribed from Eco RI digested pSP6IL-2 vector containing a 117 bp Xho I-Hind III fragment (−70 to +47 of NFAT-Tag). Hybridization was allowed to proceed at 42° C. for 16 h and samples were digested with 4 ug/ml RNase A and 160 unites/ml RNase T1 at 30° C. for 1 h. Protected fragments were run on a 5% denaturing polyacrylamide gel and exposed to XAR-5 film.

RESULTS

Figure 10:
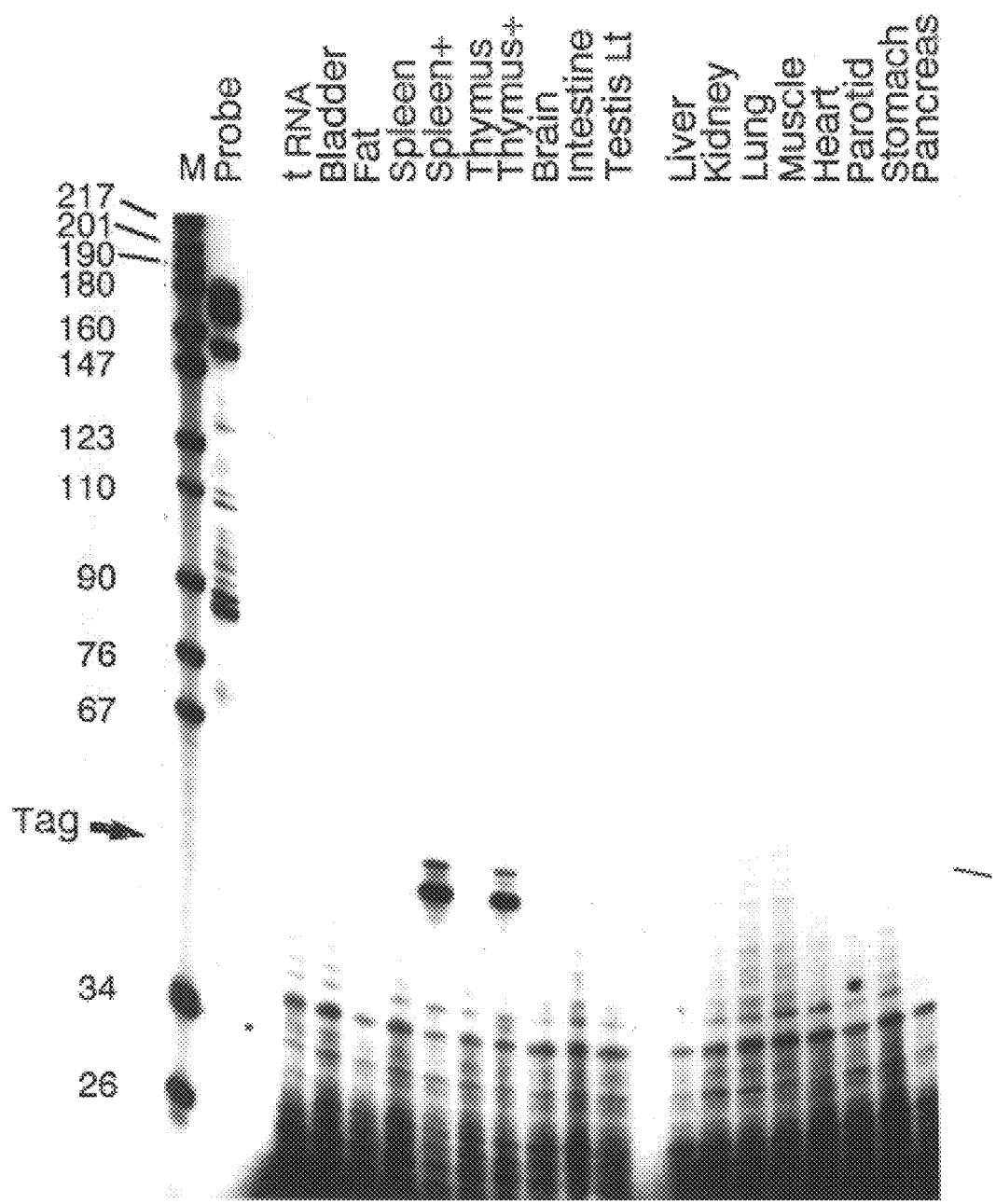
FIG. 10. NF-AT dependent T-antigen transcription levels in tissues of transgenic mice. Total RNA was prepared from tissues of a 6-week-old mouse of line Taq8 (Verweij et al. JBC 265:15788–15795 (1990). Spleen, thymus and bone marrow cells were cultured for 24 hours in the presence of ionomycin (0.6 μMl and PMA (10 ng/ml). Ten micrograms of each RNA sample was used in an RNase protection assay. As a probe we used the 176 nucleotide P-32 labeled antisense NF-AT-Tag RNA probe. Correctly initiated mRNA would yield a 47-nucleotide protected fragment. The position of the fragment (TI) is indicated by an arrow.

As shown in FIG. 10, only lymphoid cells transcribed the T antigen gene which was under the control of the tandem NF-AT binding sites. Thus, an array of NF-AT binding sites is useful for directing expression of a linked gene specifically to activated lymphoid cells.

EXAMPLE VIII

Activation of NF-AT Probably Requires Phosphorylation

Figure 11:
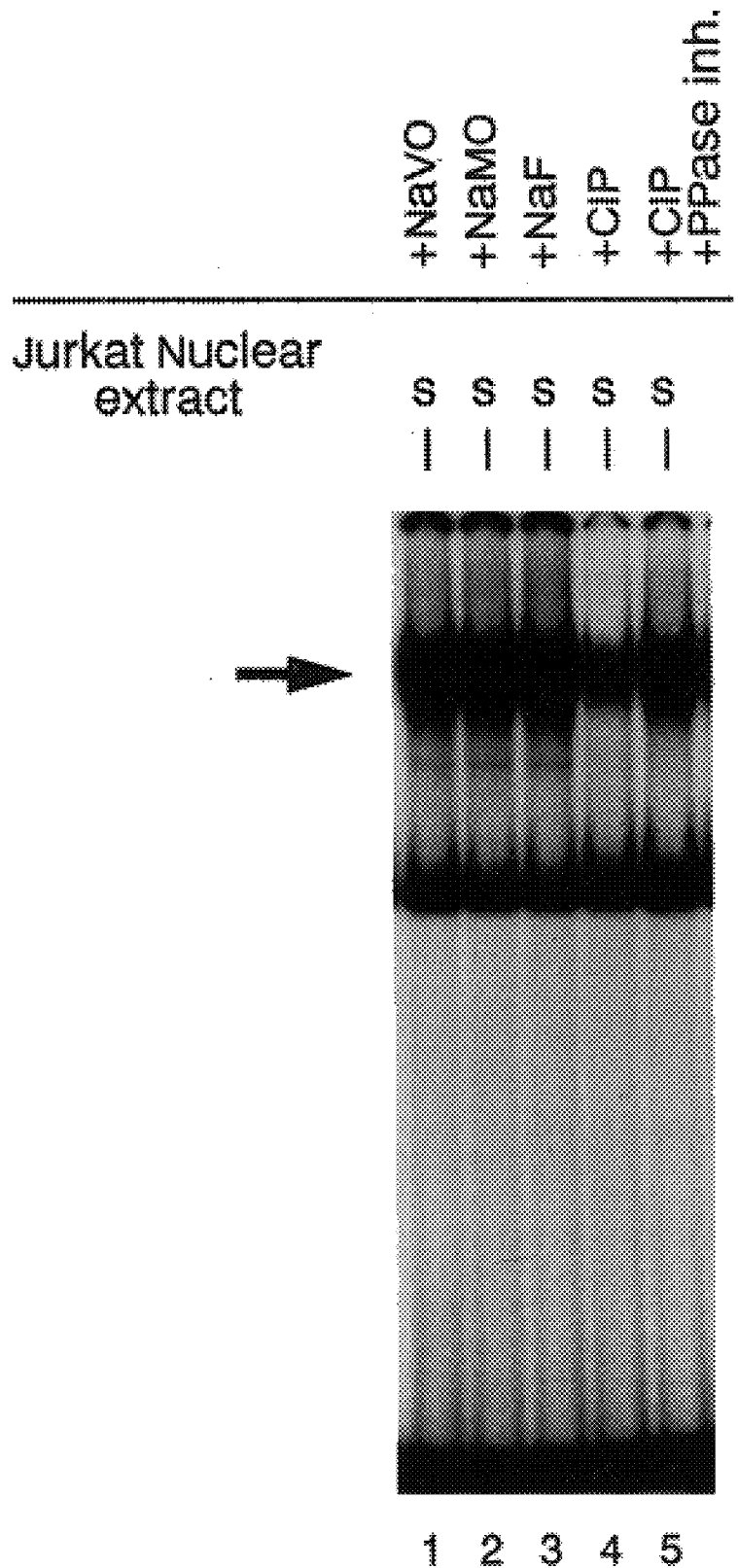
FIG. 11. Dephosphorylation of NF-AT inhibits its DNA binding. Lanes 1–5, gel mobility shift assay. Nuclear extracts (10 μg) from PMA/ionomycin stimulated Jurkat cells were incubated with several protein phosphatase inhibitors in the presence or absence of calf intestinal phosphatase. Characteristic NF-AT mobility shift in the presence of: lane 1, 200 μM sodium vanadate ($Na_2VO_4$); lane 2, 200 μM sodium molybdate ($Na_2MO_4$); lane 3, 10 mM sodium fluoride (NaF); lane 4, one unit of calf intestinal phosphatase (CIP); lane 5, one unit of calf intestinal phosphatase plus 200 μM of sodium vanadate, 200 μM sodium molybdate and 10 mM sodium fluoride. For methods see FIG. 6. The arrow indicates the NF-AT protein DNA complex.

Evidence for phosphorylation of NF-AT was obtained by treating nuclear extracts with calf alkaline phosphatase and examining the mobility of the NF-AT DNA-binding complex on nondenaturing gels. As shown in FIG. 11, dephosphorylation of NF-AT with calf intestinal phosphatase reduces its ability to associate with its DNA binding site (FIG. 11, lane 4).

Model for the Actions of FK506 and Cyclosporin A: Their Role in Preventing Nuclear Import of NF-AT A calcium stimulus induced by the antigen leads to the nuclear import of a subunit of NF-AT. Once in the nucleus, the cytosolic subunit combines with a newly induced nuclear subunit to produce a complex having both DNA-binding activity and transcriptional activity. Neither subunit alone has DNA binding activity and neither subunit alone has transcriptional activity. Cyclosporin A and FK506 prevent the import of the cytosolic component of NF-AT by either preventing the development of competence for nuclear transfer of the cytosolic component of NF-AT or by blocking the appearance of nuclear import signals for NF-AT.

REFERENCES

1. Borel, J. F., Feurer, C., Bubler, H. U. & Stahelin; H. *Agents Actions* 6, 468 (1976).
2. Sung, S. S. et al. *J. exp Med.* 168, 1539–1551 (1988).
3. Gao, E. K., Lo, D., Cheney, R., Kanagawa, O. & Sprent, J. *Nature* 336, 176–179.
4. Crabtree, G. R. *Science* 243 355–361 (1989).
5. Schreiber, S. L. *Science* 251, 283–287 (1991).
6. Hohman, R. J. & Hutlsch, T. *New Biol.* 2, 663–672 (1990).
7. Fischer, G. & Bang, H. *Biochim. biophys Acta* 828, 39–42 (1985).
8. Fischer, G., Wittman-Liebold, B., Lang, K., Kiefhaber, T. & Schmid, F. X. *Nature* 337, 476–478.
9. Handschumacher, R. E., Harding, M. W., Rice, J. & Drugge, R. J. *Science* 226, 544–547 (1984).
10. Lang, K. & Schmid, F. X. *Nature* 331, 453–455 (1988).
11. Standaert, R. F., Galat, A., Verdine, G. L. & Schreiber, S. L. *Nature* 346, 671–674 (1990).
12. Bierer, B. E., Somers, P. K., Wandless, T. J., Burakoff, S. J. & Schreiber, S. L. *Science* 250, 556–559 (1990).
13. Bierer, B. E. et al., *Proc. natn. Acad. Sci. U.S.A.* 87, 9231–9235 (1990).
14. Tropschug, M., Barthelmess, I. B. & Neupert, W. *Nature* 342, 953–955 (1989).
15. Shaw, J. P., et al., *Science* 241, 202–205 (1988).
16. Emmel, E. A. et al., *Science* 246, 1617–1620 (1989).
17. Mattila, P. S. et al., *EMBO J.* 9, 4425–4433 (1990).
18. Wiskocii, R., Weiss, A., Imboden, J., Kamin-Lewis, R. & Stobo, J. *J. Immun.* 134, 1599–1603 (1985).
19. Fiering, S. et al., *Genes Dev.* 4, 1823–1834 (1990).
20. Rosen, M. K., Standaert, R. F., Galat, A., Nakatsuka, M. & Schreiber, S. L. *Science* 248, 863–866 (1990).
21. Dumont, F. J., Staruch, M. J., Koprak, S. L., Melino, M. R. & Signal, N. H. *J. Immun.* 134, 1599–1603 (1985).
22. Duont, F. J. et al., *J. Immun.* 144, 1418–1824 (1990).
23. Karttunen, J. & Shastri, N. *Proc. natn. Acad. Sci. U.S.A.* 88, 3972–3976 (1991)
24. Kay, J. E., Doe, S. E. A. & Benzie, C. R. *Cell. Immun.* 124, 175–181 (1989).
25. Cirillo, R. et al., *J. Immun.* 144, 3891–3897 (1990).
26. Gunter, K. C., Irving, S. G., Zipfel, P. F., Siebenlist, U. & Kelley, K. *J. Immun.* 142, 3286–3291 (1989).
27. Kolestsky, A. J., Harding, M. W. & Handschumacher, R. E. *J. Immun.* 137, 1056–1059 (1986).
28. Kincaid, R. L., Takayama, H., Billingsley, M. L. & Sitkovsky, M. V. *Nature* 330, 176–178 (1987).
29. Tropschug, M., Wacter, E., Mayer, S., Schonbrunner, E. R. & Schmid, F. X. *Nature* 346, 674–677 (1990).
30. Sieklerka, J. J., Hung, S. H. Y., Poe, M., Lin, C. S. & Sigal (Signal in #21 above), N. H. *Nature* 341, 755–757 (1989).
31. Harding, W. M., Galat, A., Uehling, D. E. & Schreiber, S. L. *Nature* 341, 758–760 (1989).
32. Hunt, T. *Cell* 59, 949–951 (1989).
33. Ohtsson, H. & Edlund, T. *Cell* 45, 35–44 (1986).
34. Fried, M. G. & Crothers, D. M. *Nucleic Acids Res.* 9, 6505–6526 (1981).
35. Garner, M. M. & Revzin, A. *Nucliec Acids Res.* 9, 3047–3059 (1981).

All publications, patents, and patent applications herein are incorporated by reference. The invention now being fully described, it will be apparent to one of ordinary skill in the art that many changes and modifications can be made thereto without departing from the spirit or scope of the appended claims.

What is claimed is:

1. A composition for screening for agents having the property of inhibiting NF-AT-dependent in vitro transcription, said composition comprising:

an IL-2 G-less plasmid comprising (i) an IL-2 enhancer fused to a G-less cassette and (ii) an adenovirus major late promoter;

a nuclear extract purified from phorbol myristate acetate and ionomycin stimulated Jurkat cells, wherein the nuclear extract contains NF-AT capable of binding to an NF-AT recognition sequence consisting of -GAAAGGAGGAAAAACTGTTT-(SEQ ID NO:3) or -CAGAAGAGGAAAAATGAAGG-(SEQ ID NO:5);

poly dI-dC;

a buffered solution containing Hepes, KCl, $MgCl_2$, ATP, CTP, UTP, ($\alpha$-$^{32}$P) UTP, 3'—O-methyl GTP, RNase T1, RNase inhibitor and glycerol.

2. A composition of claim 1, further comprising a therapeutic candidate agent consisting of a macrolide.

3. A composition of claim 1, wherein said stimulated Jurkat cells are obtained by culturing Jurkat cells in the presence of ionomycin and PMA and in the presence of FK506.

4. A composition for screening for therapeutic candidate agents having the property of inhibiting NF-AT-dependent in vitro transcription, said composition comprising:

a chimeric gene comprising at least one NF-AT regulated enhancer region selected from the group consisting of -GAAAGGAGGAAAAACTGTTT-(SEQ ID NO:3); -CCAAAGAGGAAAATTTGTTT-(SEQ ID NO:4); -CAGAAGAGGAAAAATGAAGG-(SEQ ID NO:5); -TCCAGGAGAAAAAATGCCTC-(SEQ ID NO:6); -ACTTGIGAAAATACGTA-(SEQ ID NO:7); -TAAAGGAGAGAACACCAGCT-(SEQ ID NO:8); and -GCAGGGTGGGAAAGGCCTTT-(SEQ ID NO:9), linked to a polynucleotide sequence capable of being transcribed;

a nuclear extract purified from HeLa cells;

a cytoplasmic extract purified from phorbol myristate acetate and ionomycin stimulated Jurkat cells;

poly dI-dC;

a buffered solution containing Hepes, KCl, $MgCl_2$, ATP, CTP, UTP, ($\alpha$-$^{32}$P) UTP, 3'—O-methyl GTP, RNase T1, RNase inhibitor and glycerol.

5. A composition of claim 4, further comprising a therapeutic candidate agent consisting of a macrolide.

6. A composition for screening for putative immunosuppressants, said composition comprising:

a nuclear extract purified from HeLa cells;

a cytoplasmic extract purified from phorbol myristate acetate and ionomycin stimulated Jurkat cells; and a polynucleotide containing an NF-AT binding site sequence selected from the group consisting of:
-GAAAGGAGGAAAAACTGTTT-(SEQ ID NO:3); -CCAAAGAGGAAAATTTGTTT-(SEQ ID NO:4); -CAGAAGAGGAAAAATGAAGG-(SEQ ID NO:5); -TCCAGGAGAAAAAATGCCTC-(SEQ ID NO:6); -AAAACTTGIGAAAATACGTA-(SEQ ID NO:7); -TAAAGGAGAGAACACCAGCT-(SEQ ID NO:8); and -GCAGGGTGGGAAAGGCCTTT-(SEQ ID NO:9).

7. A composition of claim 6, further comprising a macrolide.

* * * * *